US008313742B2

(12) United States Patent
Kadiyala et al.

(10) Patent No.: US 8,313,742 B2
(45) Date of Patent: Nov. 20, 2012

(54) CELL-CONTAINING BONE GRAFT MATERIAL

(75) Inventors: Sudhakar Kadiyala, South Easton, MA (US); Scott P. Bruder, Sudbury, MA (US)

(73) Assignee: DePuy AcroMed, Inc., Raynham, MA (US)

( * ) Notice: Subject to any disclaimer, the term of this patent is extended or adjusted under 35 U.S.C. 154(b) by 878 days.

(21) Appl. No.: 10/109,946

(22) Filed: Mar. 29, 2002

(65) Prior Publication Data

US 2003/0185803 A1 Oct. 2, 2003

(51) Int. Cl.
*A61F 2/28* (2006.01)
*C12N 5/00* (2006.01)
(52) U.S. Cl. .................... 424/93.7; 424/577; 623/23.51; 623/23.61; 623/23.63
(58) Field of Classification Search .................. 424/93.7, 424/577
See application file for complete search history.

(56) References Cited

U.S. PATENT DOCUMENTS

| | | | |
|---|---|---|---|
| 5,733,545 A * | 3/1998 | Hood, III | 424/93.72 |
| 5,766,951 A | 6/1998 | Brown | |
| 5,811,094 A * | 9/1998 | Caplan et al. | 424/93.7 |
| 5,811,904 A | 9/1998 | Tajima et al. | |
| 5,824,084 A * | 10/1998 | Muschler | 128/898 |
| 5,904,717 A | 5/1999 | Brekke et al. | |
| 5,914,121 A | 6/1999 | Robey et al. | |
| 5,948,426 A | 9/1999 | Jefferies | |
| 6,013,067 A | 1/2000 | Fibbe et al. | |
| 6,049,026 A | 4/2000 | Muschler | |
| 6,723,131 B2 * | 4/2004 | Muschler | 623/23.51 |
| 7,172,629 B2 | 2/2007 | McKay | |
| 2001/0000751 A1 | 5/2001 | Schmitz | |
| 2002/0022885 A1 | 2/2002 | Ochi | |
| 2002/0161449 A1 | 10/2002 | Muschler | |

FOREIGN PATENT DOCUMENTS

| | | |
|---|---|---|
| AU | 2006200113 | 2/2006 |
| JP | 2001129079 | 5/2001 |
| WO | 97/40137 | 10/1997 |
| WO | 9740137 | 10/1997 |
| WO | 98/00174 | 1/1998 |
| WO | 99/59500 | 11/1999 |
| WO | WO 01/20999 A1 | 3/2001 |
| WO | 02/068010 A1 | 9/2002 |

OTHER PUBLICATIONS

Merriam-Webster Online definition of "physiological" at http://m-w.com/cgi-bin/dictionary?book=Dictionary&va=physiologic&x=17&y=13.*
Merriam-Webster Online definition of "fraction" at http://m-w.com/cgi-bin/dictionary?book=Dictionary&va=fraction&x=11&y=17.*
http://www.uq.edu.au/vdu/HDUHaemostasis.htm.*
Marx et al, "Platelet-rich Plasma: Growth factor enhancement for bone grafts" Oral Surgery, Oral Medicine, Oral Pathology, Jun. 1998, vol. 85, No. 6, pp. 638-646.*

Yee. Ted C. & Crosby, Lynn A.; Arthoscopic Ankle Fusions Utilizing Bone Marrow and Demineralized Bone Matrix: A Case Report; Nebraska Medical Journal; Sep. 1994.
Bab, I.; Ashton, B.A.; Syftestad, G.T.; Owen, M.E.; Assessment of an in vivo Diffusion Chamber Method as a Quantitative Assay for Osteogenesis; Calcified Tissue International; 1984 36:77-82.
Walsh, W.; Nicklin, S.; Loefler, A.; Yu, Y.; Arm D.; Gillies, M.; Autologous Growth Factor Gel (AGF) and Spinal Fusion; 47th Annual Meeting, Orthopaedic Research Society, Feb. 25-28, 2001, San Francisco, CA.
Tenenbaum. H.C.; Cellular Origins and Theories of Differentiation of Bone-forming Cells; Mount Sinai Hospital Research Institute and Faculty of Dentistry, University of Toronto, Toronto, Canada.
Majors, Alana K.; Boehm, Cynthia A.; Nitto, Hironori: Midura, Ronald J.; Muschler, Geroge F.; Characterization of Human Bone Marrow Stromal Cells with Respect to Osteoblastic Differentiation; Journal of Orthopaedic Research; 15:546-557 The Journal of Bone and Joint Surgery, Inc., 1997 Orthopaedic Research Society.
Harada, K.; Oida, S.; Sasaki, S.; Chondrogenesis and Osteongenesis of Bone Marrow-derived Cells by Bone-inductive Factor; Bone, 9, 177-183 (1988).
Salama, R.; Weissman, S.L.; The Clinical Use of Combined Xenografts of Bone and Autologous Red Marrow; J. Bone Joint Surg Br Feb. 1978; vol. 60-B(1): 111-115.
Matsukura, Y.; Concentration of Bone Marrow Derived Osteoprogenitors for Spinal Fusion; Department of Radiology, The Cleveland Clinic Foundation, Am. Soc. for Bone and Min Res. 22nd Ann Mtg Abst M193, Sep. 25, 2000.
Kadiyala, S.; Young, R.G.; Thiede, M.A.; Burder, S.P.; Culture Expanded Canine Mesenchymal Stem Cells Possess Osteochondrogenic Potential in Vivo and in Vitro; Cell Transplationation, vol. 6, No. 2, 125-134, 1997.
Connolly, John; Guse, Roy; Lippiello, Louis; Behne, Robert; Development of an Osteogenic Bone-Marrow Preparation; The Journal of Bone and Joint Surgery, 1998.
Mardon, Helen J.; Bee. James; Von Der Mark, Klause; Owen, Maureen; Development of osteogenic tissue in diffusion chambers from early precursor cells in bone marrow of adult rats; Cell and Tissue Research, 1987 250:157-165.
Ashton, B.A., Eaglesom, C.C.; Bab, I.; Owen, M.E.; Distribution of fibreoblastic colony-forming cells in rabbit bone marrow and assay of their osteogenic potential by an in vivo diffusion chamber method; Calcif. Tissue Int. Jan. 1987; 36 (1):83-6.
Ashton. B.A.; Allen, T.D.; Howlett, C.R.; Eaglesom, C.C.; Hattori, A.; Owne, Maureen; Formation o fBone and Cartilage by Marrow Stromal Cells in Diffusion Chambers in Vivo; Clinical Orthopaedics and Related Research; No. 151; Sep. 1980.

(Continued)

*Primary Examiner* — Allison Ford

(57) ABSTRACT

This invention relates to a musculoskeletogenic MSG graft composite made from whole bone marrow aspirate BMA having native levels of musculoskeletal progenitor cells MSPCs, comprising:
a) a suspension of fractionated BMA comprising:
i) MSPCs present at a level greater than their native level in whole BMA, and
ii) red blood cells RBCs present at a level less than their native level in whole BMA, and
b) a porous sterile matrix having an average pore size of at least 20 µm.

7 Claims, No Drawings

OTHER PUBLICATIONS

Ashton, Bab I.; Gazit, D.; Marx, G. Williamson, MC; Owne, ME; Kinetics and differentiation of marrow stromal cells in diffusion chambers in vivo; J Cell Sci Aug. 1987:84:139-51.

Ohgushi, Hajime; Okumura. Motoaki; Tamai, Susumu; Shors, Edwin C.; Caplan, Arlnold I.; Marrow cell induced osteogenesis in porous hydroxyapatite and tricalcium phosphate: A comparative histomorphometric study of ectopic bone formation; Journal of Biomedical Materials Research, vol. 24, 1563-1570 (1990).

Caplan, Arnold I.; Bruder. Scott P.; Mesenchymal stem cells: building blocks for molecular medicine in the 21$^{st}$ century, TRENDS in Molecular Medicine vol. 7 No. 6, Jun. 2001.

Bruder, Scott P.; Jaiswal, Neelam; Ricalton, Nancy S.; Mosca, Joseph D.; Kraus. Karl H.; Kadiyala Sudha; Mesenchymal Stem Cells in Osteobiology and Applied Bone Regeneration; Clinical Orythopaedics and Related Research, No. 355S, pp. S247-S256, 1998.

Budenz, Richard W.; Bernard, George W.; Osteogenesis and Leukopoiesis Within Diffusion-Chamber Implants of Isolated Bone Marrow Subpopulations; The American Journal of Anatomy 159:455-474 (1980).

Garg, N. K.; Gaur, S.; Percutaneious Autogenous Bone-Marrow Grafting in Congenital Tibial Pseudarthrosis; The Journal of Bone and Joint Surgery; vol. 77-B, No. 5, Sep. 1995.

Healey. John H.; Zimmerman, Peter A.; McDonnell, Jessop M.; Lane, Joseph M.; Percutaneous Bone Marrow Grafting of Delayed Union and Nonunion in Cancer Patients; Clinical Orthopaedics and Related Research; No. 256; Jul. 1990.

Haynesworth, S.E.; Kadiyala, S.; Liaang, L; Bruder, S.P.; Abstract: Platelet Effects on Human Mesenchymal Stem Cells; Orthopaedic Research Society, 48$^{th}$ Annual Meeting; Dallas, TX/Feb. 10-13, 2002.

Salama, R.; Burwell. R. Geoffrey; Dickson, I.R.; Recombined grafts of Bone and Marrow The Beneficial Effect upon Osteogenesis of Impregnating Xenograft (Heterograft) Bone with Autologous Red Marrow; The Journal of Bone and Joint Surgery; vol. 55B, No. 2, May 1973.

Tiedeman, Jeffrey J.; Connolly, John F.; Strates, Basil S.; Lippiello, Lous; Treatment of Nonunion by Percutaneous Injection of Bone Marrow and Demineralized Bone Matrix; Clinical Orthopaedics and Related Research; No. 268, Jul. 1991.

Ragni, P.; Lindholm. T. Sam; Lindholm. Tom C.; Vertebral Fusion and Dynamics in the Thoracic and Lumbar Spine Induced by Allogenic Demineralized Bone Matrix Combined with Autogenous Bone Marrow: Ital J Orthop Traumatol, Jun. 1987, vol. 13, No. 12, pp. 241-251.

Goshima, "Ectopic Bone Formation by Composite Graft of Culture-Expanded Human Marrow Cells and Porous Calcium Phosphate Ceramic" *English abstract*, Nippon Seikelgeka Gakkai Zasshi Jan. 1991; 65(1):34-43.

Letter dated Jan. 30, 2007 to Thomas DiMauro from Heslen, Rothenberg, Farley & Mesiti.

Weiss et al., Platelet Aggregation, Hematology, 3rd Edition, pp. 1673-1674, Chapter A43, McGraw Hill, 1983.

Letter to Thomas DiMauro from Nicholas Mesiti of Heslin Rothenberg Farley and Mesiti regarding U.S. Appl. No. 10/109,946, dated Mar. 26, 2004.

Bruder, "Identification and Characterization of a Cell Surface Differentiation Antigen on Human Osteoprogenitor Cells", Trans. Orthop. Res. Soc., 1996, vol. 21, p. 574.

Bruder, "Monoclonal Antibodies Reactive With Human Osteogenic Cell Surface Antigens", Bone, vol. 21, pp. 225-235, Elsevier.

Fleming, "Monoclonal Antibody Against Adult Marrow-Derived Mesenchymal Stem Cells Recognizes Developing Vasculature in Embryonic Human Skin", Development Dynamics, 1998, vol. 212, pp. 119-132, Wiley-Liss, Inc.

Stewart, "Co-Expression of the Stro-1 Antigen and Alkaline Phosphatase in Cultures of Human Bone and Marrow Cells", ASBMR 18th Annual Meeting, Journal of Bone and Mineral Research, vol. 11 Supp., pp. S142, 1996.

Wan, Allogenic Peripheral Blood Derived Mesenchymal Stem Cells (MSCs) Enhance Bone Regeneration in Rabbit Ulna Critical-Sized Bone Defect Model, Journal of Orthopaedic Research, Apr. 2006, pp. 610-618, Orthopaedic Research Society Published by Wiley Periodicals, Inc.

* cited by examiner

CELL-CONTAINING BONE GRAFT MATERIAL

BACKGROUND OF THE INVENTION

Bone marrow has been considered as a source of musculoskeletogenic ("MSG") components for producing autologous graft materials useful in the repair/regeneration of musculoskeletal tissues such as bone, cartilage and tendon. Bone marrow aspirate ("BMA") is typically obtained from the patient during surgery by well known techniques and includes the following components set out in Table I below:

TABLE I

| BMA Component | Volume Fraction |
|---|---|
| Plasma | 40-45 vol % |
| Buffy Coat Fraction (BCF) | 1-10 vol % |
| Red Blood Cells | 45-50 vol %. |

The BCF comprises all of the nucleated bone marrow cells ("NBMC"), platelets, proteins and molecules contained within the density band of materials residing between the serum and red blood cell portions of the BMA, as determined by conventional centrifugation of whole BMA. The NBMC component of the BCF typically comprises the following compliment of cell types and approximate concentrations as set out in Table II:

TABLE II

| NBMC Type | Relative Native Concentration (Approximate) (cells/total NBMC cells) | Absolute Native Concentration. (Approximate) (cells/ml BMA) |
|---|---|---|
| Musculoskeletal Precursor Cells MSPCs | <1% | <200,000 |
| Nucleated Hematopoitic Cells (HCs) | 95-99% | $20 \times 10^6$ |
| Reticulocytes (RCs), | <0.1% | <20,000 |
| Endothelial Cells (ECs) | <0.1% | <20,000. |

In a first conventional method of using bone marrow for its osteogenic capacity, whole or "fresh" bone marrow is either used directly as a graft material or is combined with a matrix material to produce a bone graft composite. For example, Harada, *Bone* 9 (1988) 177-183, disclosed a composite comprising whole BMA within a porous matrix of demineralized bone matrix (DBM) contained within a diffusion chamber. However, the diffusion chamber has a semi-permeable membrane that allows the passage of nutrients, and so prevents the influx of cellular components and vasculature critical to osteogenesis. Moreover, as the success of this procedure depends in part upon the native levels of MSPCs in the bone marrow, and such native levels of MSPCs in the patient's bone marrow can sometimes be depleted, the widespread utility of this procedure is limited. Moreover, even at relatively normal native levels of MSPCs, these cells are relatively scarce in fresh bone marrow and so the osteogenic potential of whole bone marrow per se is thereby limited.

In a second conventional method, plasma is removed from whole bone marrow, and the remaining mixture comprising the BCF and red blood cells is either used directly as a graft material or combined with a matrix material to produce a bone graft composite. For example, Ohgushi, *J.Biomed. Mat.Res.* (1990), 24:1563-70 disclosed centrifuging BMA, and using the remaining red cell/BCF fraction as an interstitial fluid within a porous matrix of HA or TCP. As plasma comprises about 45 volume percent ("vol %") of bone marrow aspirate, this method produces only slightly elevated levels of MSPCs (i.e., less than a 2-fold increase) relative to the native level of MSPCs in the fresh bone marrow. In addition, the suspension essentially lacks the soluble or insoluble factors found in plasma such as albumin. Lastly, the presence of red blood cells ("RBCs") in this composition may also cause inhibition of MSPC activity through steric hinderance of surface accessibility and high local iron concentrations following RBC lysis.

In a third conventional method, the buffy coat of the BMA is isolated from the plasma and red blood cell fractions. For example, Connolly et al., *JBJS* (1989) pp. 684-691, sought to "optimize" the osteogenic potential of BMA, and disclosed isolating fractions of BMA and then using those fractions as graft material in diffusion chambers. Connolly used the following isolation methods:

a) simple centrifugation followed by removal of the supernatant (i.e., serum) fraction,
b) isopyknic centrifugation, followed by separate removal of the light cell (buffy coat) and red cell fractions, and
c) unit gravity centrifugation, followed by separate removal of the light cell (buffy coat) and red cell fractions.

Although Connolly reported that the concentrated light cell (buffy coat) fraction produced by isopyknic centrifugation yielded the greatest level of calcium production within the diffusion chamber, Connolly chose the combined red cell/light cell fraction produced by simple centrifugation (i.e., light cell and red cell fractions) for further study. Moreover, Connolly did not provide a porous substrate carrier material within the diffusion chamber. Lastly, Connolly's examples that utilized the BCF also eliminated the factors present in the plasma fraction of the BMA.

In a fourth conventional method the isolated buffy coat is further fractionated. For example, Budenz et al., *Am.J.Anat.*, 159 (1980), pp. 455-474, discloses isolating fractions of the BCF of bone marrow aspirate in high concentrations, and inserting that concentrated fraction into a diffusion container which is then implanted into rats. The limitations associated with diffusion chambers has been discussed above. Budenz does not disclose using the entire BCF fraction in toto. Lastly, Budenz does not disclose a porous substrate carrier material within the diffusion chamber.

In a fifth conventional method, an enriched fraction of MSPCs (relative to all other NMBCs) is combined with a matrix material to produce a bone graft. MSPCs can be enriched by a variety of well-known methods. For example, U.S. Pat. No. 6,049,026 ("Muschler '026") discloses passing bone marrow aspirate through a matrix capable of selectively retaining MSPCs. This process produces a composite having enriched amounts of MSPCs (i.e., up to 2.8-fold higher than the native MSPC level found in the same volume of autologous bone marrow). However, this composite is also devoid of the cells, molecules and proteins present in BMA that are not retained by the substrate, and is depleted of other constituents found in BMA, which do not have a high affinity for the substrate. In addition, the process disclosed in Muschler '026 for enriching the MSPCs is inefficient, routinely failing to capture between about 33% and 56% of the MSPCs present in the BMA. Moreover, Muschler discloses optionally washing the MSPC-laden substrate in order to remove any cells which have been only loosely retained, thereby reducing even further the presence of cells which do not have a high affinity for the substrate. Muschler discloses optionally adding to the composite various discrete bioactive constituents such as platelets, cell adhesion molecules (such as collagens), growth factors (such as BMPs), antibodies (such as STRO-1).

Some investigators disclosed in vitro culturing of whole or fractionated BMA in an effort to obtain a plentiful and pure population of MSPCs. For example, Majors. *J. Orthop. Res.* (1997) 15:546-557, disclosed isolating the BCF of the BMA by centrifugation, culturing the BCF to produce an enriched MSPC population, and staining the MSPCs as a means for assaying the osteoblastic progenitor population within BMA.

PCT Published Patent Application No. 97/40137 ("Kadiyala") discloses compositions and methods for augmenting bone formation by administering isolated human mesenchymal stem cells with a ceramic material or matrix or by administering human mesenchymal stem cells; fresh, whole marrow or combinations thereof in a resorbable biopolymer that supports their differentiation into their osteogenic lineage. Kadiyala contemplates the delivery of (i) isolated, culture expanded, human mesenchymal stem cells; (ii) freshly aspirated bone marrow; or (iii) their combination in a carrier material or matrix to provide for improved bone fusion area and fusion mass, when compared to the matrix alone. In Example V, discloses a composition comprising a collagen/ceramic composite mixed 50:50 with fresh bone marrow nucleated cells that had been concentrated ten-fold by centrifugation and buffy coat isolation (BMC). The procedure required for producing the culture-expanded, purified MSPCs is a long and arduous one (often requiring about about 21 to 56 days), and so can not be performed intra-operatively. U.S. Pat. No. 5,914,121 ("Robey") discloses a composition comprising cultured MSPCs and HA/TCP powder, and optionally adding commercially-prepared fibrinogen and thrombin to the composition for the purpose of making fibrin glue.

A few investigators have reported supplementing porous matrices containing concentrated MSG fractions with whole BMA. For example, Walsh, "Autologous Growth Factor Gel (AGF) And Spinal Fusion" $47^{th}$ Annual Meeting, ORS, February 2001, discloses a graft material comprising a HAP porous matrix, PRP and whole BMA. However, Walsh does not disclose a concentrated, physiologic fraction of fractionated bone marrow aspirate BMA, only whole BMA.

Matsukura, "Concentration of Bone Marrow Derived Osteoprogenitors for Spinal Fusion", Am. Soc. Bone. Min. Res. $22^{nd}$ Annual Meeting Abstracts, September 2000, discloses a graft material comprising an enriched fraction of MSPCs, whole bone marrow and a porous matrix. Matsukura does not disclose a concentrated, physiologic fraction of fractionated bone marrow aspirate BMA. The enriched fraction of MSPCs taught in Matsukura is not a suspension and so is depleted of the soluble constituents present in the corresponding physiologic fraction of BMA having high levels of MSPCs.

A US Patent Application entitled, "Composite Bone Marrow Graft Material With Method and Kit" ("Muschler II") discloses a composite bone marrow graft material comprising a porous biocompatible implantable matrix, an enriched population of progenitor cells (MSPCs) and a clot material. The clot material can be a blood clot formed from blood, a bone marrow clot, a platelet gel, a platelet concentrate, fibrin clot or a fibrin glue. Since the enriched population of MSPCs is formed by the method taught in Muschler I and so (like Matsukura) is depleted of the soluble constituents present in the corresponding physiologic fraction of BMA having high levels of MSPCs, Muschler II does not disclose a concentrated, physiologic fraction of fractionated bone marrow aspirate BMA.

In sum, the conventional technologies either:
a) use whole marrow as a source of MSPCs, and so suffer from low MSPC concentrations (such as Walsh),
b) seek to enrich MSPCs by wholly eliminating other MSG constituents found in the BMA, and so do not have some of the supplemental MSG constituents present in BMA (such as Muschler I),
c) introduce isolated supplemental MSG constituents into composites having enriched levels of MSPCs, and so have only partially provided the supplemental MSG constituents present in BMA (such as Muschler I), or
d) add merely whole BMA into composites having enriched levels of MSPCs and so have only unenhanced levels of the supplemental MSG constituents (such as Muschler II and Matsukura)

Moreover there is only a sporadic appreciation in the prior art of the advantages of combining MSG fractions with a porous matrix. For example, there is no disclosure in the prior art of a combination of a physiologic fraction of BMA in combination with a matrix and supplemented with whole BMA.

SUMMARY OF THE INVENTION

The present inventors believe that composite tissue repair graft materials having improved musculoskeletogenic capabilities should comprise not only enhanced MSPC levels, but also suitable levels of other MSG constituents found in BMA that are thought to play a role in the tissue repair pathway. However, the present inventors have noted that the conventional procedures of concentrating MSPCs deplete or fully eliminate many of the musculoskeletogenic MSG constituents in BMA thought to play a significant role in musculoskeletogenesis. Therefore, the present inventors have concluded that, although the conventional step of concentrating MSPCs from BMA may enhance osteogenesis in one respect (by enhancing MSPC levels), it may also limit tissue repair in a second respect (depleting, and sometimes wholly eliminating, important supporting MSG constituents from BMA). Accordingly, the resulting conventional high-MSPC products possess significant disadvantages.

Accordingly, in order to solve this inadequacy in conventional bone graft materials, the present inventors have developed a number of approaches that cure the above-noted deficiencies of the prior art.

In the first approach, there is provided a musculoskeletogenic MSG graft composite made from whole bone marrow aspirate BMA having a native level of musculoskeletal progenitor cells MSPCs and a native level of red blood cells RBCs, comprising:
a) a physiologic fraction of BMA comprising:
  i) MSPCs present in the physiologic fraction at a level greater than their native level in whole BMA, and
  ii) RBCs derived from BMA present in the physiologic fraction at a level less than their native level in whole BMA, and
b) a porous sterile matrix having an average pore size of at least 20 μm.

Because the MSPC source of this approach is a fraction of BMA, it can contain higher levels of MSPCS than are present in conventional grafts (such as Harada and Walsh) using whole BMA as an MSPC source. Because the fraction has a depleted level of RBCs, its MSPCs may be more concentrated than the MSPCs in the composite of Ohgushi. Because the fraction of BMA of this composite is a physiologic fraction, it contains enhanced levels of the native compliment of cells and other soluble factors that likely play a role in musculoskeletogenesis, and so contains higher levels of supporting constituents than are found in composites possessing essentially isolated MSPCs supplemented only by whole BMA (such as Muschler and Matsukura). Accordingly, this graft solves the above-noted deficiencies of the prior art.

Moreover, this composite may be easily made by simply concentrating MSPCs from whole BMA (by, for example, retaining only the buffy coat from centrifuged BMA) and then contacting the retained MSPC-rich physiologic fraction with the porous matrix.

For the purposes of the present invention, a "physiologic fraction of bone marrow aspirate BMA" is any fraction of BMA obtainable by centrifugation of whole BMA, wherein the fraction is not further processed to separate the various constituents present in that fraction. By way of illustration, one such physiologic fraction of bone marrow aspirate BMA is the buffy coat portion. Although preferred embodiments use centrifugation as the means of obtaining the "physiologic fraction of bone marrow aspirate BMA", other processes which allow the isolation of a physiologic fraction of bone marrow aspirate BMA obtainable by centrifugation are also contemplated as being within the scope of the present invention. For example, lysis of red blood cells produces a "physiologic fraction of bone marrow aspirate BMA" comprising NBMCs, and so is cellularly equivalent to the buffy coat fraction. A "physiologic fraction of bone marrow aspirate BMA" does not include whole bone marrow aspirate, but does include dewatered BMA. The MSG constituent concentrations in a "physiologic fraction of bone marrow aspirate BMA" are greater than those found in whole BMA (i.e., they are concentrated). In accordance with the present invention, a "physiologic fraction of bone marrow aspirate BMA" has a multitude of MSG constituents present in relative amounts which are equal to those relative amounts found in any continuous segment of centrifuged BMA. It has the native compliment of MSG constituents contained within a given density band of centrifuged BMA. Since the native compliment is maintained, the "physiologic fraction of bone marrow aspirate BMA" contains not one but many constituents thought to be helpful in MSG, and in relative proportions essentially equal to that obtainable by centrifugation. By way of illustration, when the "physiologic fraction of bone marrow aspirate BMA" is the buffy coat portion of BMA, it contains all the various constituents present in Table II, and these constituents have the relative concentrations typified by those in Table II. For the purposes of the present invention, water is not considered to be a constituent of BMA, and so removing only water from a "concentrated, physiologic fraction of bone marrow aspirate BMA" does not change the nature of that fraction as a "physiologic fraction of bone marrow aspirate BMA".

DETAILED DESCRIPTION OF THE INVENTION

For the purposes of the present invention, "fresh" bone marrow is bone marrow that is unfractionated, or "whole". A "$D_{50}$ average pore size" is determined by mercury porosimetry. "Nucleated bone marrow cells" ("NBMCs") include MSPCs, nucleated hematopoeitic cells (HCs), pre-osteoblasts (POs), reticulocytes (RCs), and endothelial cells (ECs), but do not include red blood cells or platelets. "Concentrating" and "isolating" steps refer to those procedures that increase the concentration of a constituent in a volume by eliminating either water or other non-selected constituents.

For example, MSPCs may be concentrated by removing the plasma portion of a centrifuged bone marrow aspirate. A "level" of a constituent is its concentration in terms of mg/ml or cells/ml.

For the purposes of the present invention, a "depleted level" of a constituent means the constituent is present at a level that is less than its corresponding native level in autologous BMA. A composition having a depleted level of a constituent includes embodiments in which the constituent is wholly absent.

For the purposes of the present invention, an "enhanced" population of MSPCs is one that has a greater level of MSPCs than that found in the original autologous bone marrow aspirate from that individual. That is, an enhanced population of MSPCs is satisified by the condition:

$$\frac{[MSPC]_{enh}}{[MSPC]_{asp}} > 1. \quad (1)$$

For the purposes of the present invention, an "enriched" population of MSPCs means that the level of MSPCs as compared to HCs is greater in the composite bone marrow graft than in the original autologous bone marrow aspirate. That is, an enriched population of MSPCs is satisified by the condition:

$$\frac{[MSPC]_{enh}}{[HC]_{enh}} > \frac{[MSPC]_{asp}}{[HC]_{asp}}. \quad (2)$$

For the purposes of the present invention "musculoskeletal tissue" comprises bone, tendon, cartilage, ligament, muscle and periodontium. "Musculoskeletogenic grafts" include osetogenic grafts, chrondrogenic grafts and tenogenic grafts.

For the purposes of the present invention, an "adhering" material is a material that may adhere to the porous matrix material when passed through the porous matrix material.

In some embodiments, the physiologic fraction of BMA is suspended within the pores of the matrix. Since the MSPCs of this embodiment are not adhered to the surface of the matrix, but rather are simply suspended within the pores, they may be more active and closer to their physiologic developmental stage. They may also form cell aggregates.

In some embodiments, the MSPCs are present in the physiologic fraction at a level 2 times greater than their native level in whole BMA, preferably at a level 5 times greater than their native level in whole BMA. These embodiments provide an even greater concentration of this critical component of MSG.

In some embodiments, the RBCs derived from BMA are present in the physiologic fraction at a level less than 20% their native level in whole BMA, thereby allowing the MSPC-rich buffy coat to represent a large portion of the volume of the retained BMA fraction, and so allowing even higher levels of cellular MSG constituents such as MSPCs.

In some embodiments, the fractionated BMA further comprises fibrinogen present in the physiologic fraction at a level less than 20% its native level in whole BMA. Since the vast majority of fibrinogen is in the plasma volume of fractionated BMA, keeping the fibrinogen level low (by, for example, substantially removing the PPP fraction) allows the MSPC-rich buffy coat to represent a large portion of the volume of the retained BMA fraction, and so allowing even higher levels of cellular MSG constituents such as MSPCs.

In some embodiments, the whole BMA further comprises hematopoetic cells HCs at a native level, the physiologic fraction of BMA further comprises hematopoetic cells HCs, and the MSPCs present in the physiologic fraction are enriched. This embodiment may be made by selecting only a relatively MSPC-rich portion of the buffy coat, thereby providing a very high level of MSPCs in the composite. Preferably, however, the HCs are present in the physiologic fraction at a level of at least 25% of their native in whole BMA, thereby providing the composite with a near native level of HCs that act to support musculoskeletogenesis.

In some embodiments, the whole BMA further comprises platelets having a native level, and the fractionated BMA further comprises platelets present in the physiologic fraction at a level greater than their native level. If a platelet release agent (such as thrombin) is added to this composite, the thrombin can cause a release of MSG growth factors (such as TGF-β) contained within the platelets. The concentrated platelet level of this embodiment is advantageous because it will provide more of these desirable growth factors. In some embodiments, the platelets are present in the physiologic fraction at a level 2 times greater than their native level (obtainable, for example, from a physiologic fraction like PRP).

In some embodiments, the physiologic fraction consists essentially of the BMA buffy coat. This embodiment essentially maximizes the levels of the desirable NBMCs and platelets in the fraction obtainable by simple gravity-fractionation of whole BMA by substantially removing the RBC and PPP fractions of BMA.

In some embodiments, the whole BMA further comprises platelets having a native level, and the fractionated BMA further comprises platelets present in the physiologic fraction at a level less than their native level. Such an embodiment may be desirable if growth factors are added to the composite from another source, such as PRP from whole blood. In such embodiments, the platelets may be present in the physiologic fraction at a level no more than 50% of their native level.

In some embodiments, the physiologic fraction consists essentially of the NBMC fraction of the BMA buffy coat. This embodiment essentially maximizes the levels of the desirable NBMCs in the fraction obtainable by simple gravity-fractionation of whole BMA by substantially removing the RBC, PPP and platelet fractions of BMA.

In some embodiments, the HCs are present in the physiologic fraction at a level greater than their native level. This embodiment provides a higher level of this important MSG cell type without necessarily requiring MSPC enrichment.

In some embodiments, both the MSPCs and HCs are present in the physiologic fraction at a level 2 times greater than their native level. This embodiment provides high level of what are possibly the two most important cell types for MSG.

In some embodiments, the physiologic fraction further comprises growth factors released from BMA-derived platelets. Such growth factors aid in MSG.

In some embodiments, the physiologic fraction comprises fibrin.

In some embodiments, the porous matrix has a pore size of at least 50 μm. This larger average pore size provides an easier pathway for MSG cells than does a pore size of 20 μm. Preferably, the porous matrix has a pore size of at least 100 μm.

In some embodiments, the porous matrix and physiologic fraction each have a non-porous volume, wherein the volumetric ratio of the physiologic fraction to the matrix is between 1:1 and 1:20. When the ratio is at least 1:1, the physiologic fraction is present in sufficiently large amounts to assist in MSG. When the ratio is no more than 1:20, the porous matrix is present in sufficiently large amounts to form a scaffold.

In some embodiments, the whole BMA further comprises a first supporting constituent at a native level, the physiologic fraction further comprises a depleted level of the first supporting constituent, and the composite further comprises c) an MSG supplement comprising the first supporting constituent, the first supporting constituent being present in the supplement at a level greater than the depleted level of the first supporting constituent in the physiologic fraction.

In some embodiments, the physiologic fraction of BMA is a suspension, and the MSG supplement comprises a mixture selected from the group consisting of whole blood and whole BMA. This embodiment allows the MSG supplement to be obtained autologously during surgery without any further manipulation.

In some embodiments, the physiologic fraction of BMA is a suspension, and the MSG supplement comprises a physiologic faction of a mixture selected from the group consisting of whole blood and whole BMA.

In some embodiments, the MSG supplement comprises a physiologic faction of whole blood. A whole blood supplement is advantageous because it can be obtained from the patient at the point of surgery. Preferably, the physiologic fraction of whole blood comprises platelet rich plasma PRP. Concentrated growth factors can be obtained from this PRP with a minimum of manipulation.

In some embodiments, the MSG supplement comprises a physiologic fraction of whole BMA. This fraction can be obtained from the same separation step that produced the first physiologic fraction.

In some embodiments, the physiologic fraction comprises a physiologic buffy coat fraction comprising present in the physiologic fraction at a level at least 2 times greater than its native level.

Any conventional method of obtaining bone marrow aspirate may be used. In one method, percutaneous access to the anterior or posterior iliac crest is obtained through a large bore needle (i.e., Jamshidi) and syringe. Aspiration of marrow contents into a syringe pre-filled with an anticoagulant such as heparin sodium is performed while pulling the needle backward and out from its deepest point of insertion. Multiple punctures into the bone may be performed in order to obtain aspirations with the smallest amount of contamination of peripheral blood.

In some embodiments, a physiologic fraction of BMA having concentrated MSPCs is obtained by first fractionating whole BMA to obtain a fractionated BMA and then removing the undesired fractions to leave the physiologic fraction having enhanced MSPCs. Fractionation of the bone marrow aspirate may be performed by any conventional method of isolating nucleated cells, including density gradient centrifugation, osmotic lysis of particular cells (such as water to lyse red blood cells), and other methods for concentrating the active osteogenic portion of fresh bone marrow. In one preferred method, the aspirate is first centrifuged at 500 g for 5-10 minutes, resulting in a fractionated aspirate having a plasma fraction, a whole buffy coat portion comprising an NMBC-rich portion and a platelet rich portion, and a RBC fraction. Within the NMBC-rich portion is a fraction having an enriched level of MSPCs. The plasma, PRP, and RBC fractions are then substantially removed by drawing off, thereby essentially isolating NMBC-rich portion. Optionally, a selected fraction or fractions of the whole buffy coat fraction may also be removed to leave a fraction having an enriched level of MSPCs.

Preferably, the MSPCs in the physiologic fraction of BMA are present in the physiologic fraction at a level of at least about 2 times its native level. This enhanced level may be achieved by removing at least about 90% of either the plasma or red blood cells from the fractionated bone marrow aspirate. More preferably, the MSPCs are present at a level of at least 5 times its native level. This enhanced level may be achieved by removing at least about 90% of both the plasma and red blood cell fractions from the fractionated bone marrow aspirate. More preferably, the MSPCs are present in the physiologic fraction at a level of at least 10 times their native level. This enhanced level may be achieved by removing at least about 99% of both plasma and red blood cells from fractionated bone marrow aspirate.

Preferably, the HC of the physiologic fraction is present in the physiologic fraction at a level of at least about 2 times its native level. This level may be achieved by removing at least about 90% of either the plasma or red blood cells from the fractionated bone marrow aspirate. More preferably, the HC is present in the physiologic fraction at a level of at least 5 times its native level. This level may be achieved by removing at least about 90% of both serum and red blood cells from the fractionated bone marrow aspirate. More preferably, the HC is present at a level of at least 15 times its native level. This level may be achieved by removing at least about 99% of both serum and red blood cells from the fractionated bone marrow aspirate.

Without wishing to be tied to a theory, it is believed that HCs play an important support role to MSPCs in osteoblast formation by secreting a variety of growth factors and cytokines as well as stimulating differentiation through direct cell to cell contact, and so are desirably present in the CTCPC-rich suspensions at elevated levels. Accordingly, in one embodiment, the present invention provides an autologous graft composite for grafting in a patient having native levels of MSPCs and HCs, the graft composite comprising:
 a) a suspension comprising MSPC and HC cell types, wherein each of the MSPC and HC cell types are present in a concentration at least 2 times greater than their native levels, and the suspension excludes at least a portion of the nucleated cells found in bone marrow,
 b) a porous matrix having an average pore size of at least 20 µm.

Accordingly, in one embodiment, the present invention provides an autologous graft composite for grafting in a patient, the graft composite comprising:
 a) a whole buffy coat portion of whole bone marrow,
 b) at least a portion of a plasma portion of whole bone marrow, and
 c) a porous matrix having an average pore size of at least 20 µm.

In that the porous matrix component of the composite of the present invention has a $D_{50}$ average pore size, as determined by mercury porosimetry, of at least 20 um, its porosity is sufficient to allow nucleated bone marrow cells to flow there through (i.e., it is a scaffold). The ability of these nucleated cells to pass out of the matrix (and for native nucleated cells to pass into the matrix) allows the MSG to take place smoothly and seamlessly both in and around the substrate. In contrast, the diffusion container technology of Harada does not provide seamless ostoegenesis.

Preferably, the matrix is made from a biocompatible, implantable graft material. Preferably, it is also resorbable. In some embodiments, the material has a charged surface. Preferably, the composite comprises between about 5-50 vol % matrix and between about 50-95 vol % suspension disposed within the pores formed by the matrix. If the volume fraction of the matrix is less than about 5 vol % (excluding its porosity), then the effect of the matrix as a scaffold is not significant.

Examples of biocompatible, implantable graft materials having a charged surface include ceramics comprising calcium phosphate such as, for example, hydroxyapatite or tricalcium phosphate; as well as demineralized bone matrix; or mineralized bone matrix. Other suitable graft materials include polylactic acid, polyglycolic acid, polygalactic acid, polycaprolactone, polyethylene oxide, polypropylene oxide, polysulfone, polyethylene, and polypropylene. Other suitable graft materials are hyaluronic acid, which may be purified with or without crosslinking, bioglass, gelatin and collagen. Particularly suitable graft materials include, for example, isolated mineralized cancellous bone sections, powders or granules of mineralized bone, demineralized cancellous bone sections, powders or granules of demineralized bone, guanidine-HCl extracted demineralized bone matrix, sintered cortical or cancellous bone, coralline hydroxyapatite sold by Interpore under the trade name Interpore 500™, or Interpore 200™, ProOsteon 500R™ and granular ceramics such as that incorporated into the bone graft substitute Collagraft™ sold by Zimmer™, or filamentous collagen or gelatin sponges such as Gelfoam™ or Helistat™.

In some embodiments, cell adhesion molecules are bound to the surface of the matrix. The term "cell adhesion molecules" refers collectively to laminins, fibronectin, vitronectin, vascular cell adhesion molecules (V-CAM), intercellular adhesion molecules (I-CAM), tenascin, thrombospondin, osteonectin, osteopontin, bone sialoprotein, and collagens. Optionally, the matrix has growth factors bound to the surface thereof. As used herein, the term "growth factors" encompasses any cellular product that modulates the growth or differentiation of other cells, particularly connective tissue progenitor cells. Growth factors include, but are not limited to, isoforms of platelet-derived growth factors (PDGF), fibroblast growth factors, epithelial growth factors, isoforms of TGF-β, insulin-like growth factors, and bone morphogenic proteins.

Optionally, the matrix has antibodies that have affinity for connective tissue progenitor stem cells bound to the surface thereof. Suitable antibodies, include by way of example, STRO-1, SH-2, SH-3, SH4, SB-10, SB-20, and antibodies to alkaline phosphatase. Such antibodies are described in Haynesworth et al., *Bone* 13:69-80,1992a; Bruder, S. et al. *Trans Ortho Res Soc* 21:574; 1996; Haynesworth, S. E., et al. *Bone* 13:69-80; 1992; Stewart, K., et al, *J Bone Miner Res* 11 (Suppl.):S142;1996; Flemming J E, et al., in "Embryonic Human Skin. Developmental Dynamics" 212:119-132, 1998, and Bruder S P, et al,. *Bone* 21(3): 225-235, 1997.

In some embodiments, the matrix has a sufficient number of pores or passageways so that the total accessible surface area of the substrate is at least five times greater than a solid object having the same external dimensions. Thus, the preferred total surface area can be achieved by using a substrate which comprises a mass of powder, a mass of granules, a mass of fibers, or a highly porous block of substrate material. Preferably, the average pore size in the matrix is greater that 20 µm, more preferably greater than 50 µm, most preferably greater than 100 µm.

Also in accordance with the present invention, there is provided a process wherein whole bone marrow aspirate is centrifuged to provide a fractionated aspirate; the red blood cells and plasma are substantially removed from the aspirate to obtain a physiologic fraction of BMA comprising a whole buffy coat suspension having nucleated bone marrow cells (NBMC) present in the physiologic fraction at a concentration 2 times (and preferably at least 5 times) their native level; and this whole buffy coat suspension is then placed into a suitably porous matrix. In this case (claim A), the present invention provides a composite comprising:
- a) a physiologic fraction comprising a whole nucleated bone marrow cell NBMC suspension in which both MSPC and HC cell types are present in a cell population between 2 and 9 times greater than their native levels, and
- b) a porous matrix, wherein the matrix has an average pore size of at least 20 um.

For the purposes of the present invention, a "whole NBMC suspension" comprises a suspension in which the ratio MSPC's to HC's is within 50 percentage points of that native ratio of MSPC:HC present in the autologous whole bone marrow aspirate. In other words, the whole buffy coat suspension satisfies the following relation:

$$0.50 \cdot \frac{[MSPC]_{asp}}{[HC]_{asp}} < \frac{[MSPC]_{susp}}{[HC]_{susp}} < 1.50 \cdot \frac{[MSPC]_{asp}}{[HC]_{asp}}. \quad (3)$$

Preferably, the ratio of MSPC:HC in the suspension is within 25% of that in the native aspirate, more preferably within 5%.

A whole NBMC suspension is advantageous because it contains concentrated amounts of two of the major BMA-derived cell types thought to play a role in MSG.

Optionally, the platelet component of the fractionated BMA is also removed during the above-described process to provide an essentially isolated whole NBMC suspension. When this isolated whole NBMC suspension is combined with a suitable matrix, the resulting composite comprises:
- a) an essentially isolated whole NBMC suspension coat fraction in which both MSPC and HC cell types are present in a cell population between 2 and 9 times greater than their native levels, and
- b) a porous sterile implantable matrix, wherein the matrix has an average pore size of at least 20 um.

The resulting composite for use in autologous bone grafting comprises:
a) a physiologic fraction of BMA comprising:
   i) an enriched level of connective tissue progenitor cells MSPCs, and
   ii) hematopoeitic cells (HCs) having a level which is at least 25% of its native level, and
b) a porous biocompatible implantable matrix having an average pore size of at least 20 um.

Preferably, the above composite further comprises a gelling agent useful for holding the composite together. In some embodiments, the gelling agent is a clotting agent comprising an amount of fibrinogen which, when added to the composite, is present in the composite at a concentration of at least 0.1 mg/cc of the composite, more preferably at least 0.5 mg/cc. Preferably, the clotting agent is selected from the group consisting of platelet poor plasma, platelet rich plasma and whole bone marrow aspirate. Typically, the clotting agent is activated by an activator such as thrombin. The activator may be mixed into the composite prior to its placement at a wound site, or placed simultaneously with the composite at the wound site. In some embodiments, the fibrinogen is present in the physiologic fraction of BMA. In others, it is added as a separate component. In some embodiments, the gelling agent is collagen.

As noted above, it is believed that conventional concentration of the NBMC fraction (for example, by centrifugation followed by separation) within BMA leading to enhanced MSPCs may also lead to an undesirable depletion in the resulting concentrated component of at least some of the following native constituents within BMA, at least some of which may play a supporting role in musculoskeletogenesis. Some of these native supporting constituents are believed to be:
- a) plasma-based constituents, such as:
  i) plasma proteins (both adhering and non-adhering) such as VCAM; and
  ii) soluble growth factors such as EGF and TGF-β,
- b) buffy coat-based constituents, such as:
  i) cells other than MSPC such as HCs and OBs;
  ii) proteins and molecules which either are nonadhering (such as RDGF) or do not reside in the MSPC-rich fraction of the buffy coat obtainable by centrifugation, such as those interleukins secreted by HCs;
  iii) platelets,
  iv) growth factors released by platelets such as TGF-β and PDGF, and
- c) red blood cell-based constituents, such as oxygen-binding hemoglobin.

Therefore, in a second approach, there is provided a musculoskeletogenic MSG graft mixture made from whole bone marrow aspirate BMA having native levels of musculoskeletal progenitor cells MSPCs and a first supporting constituent, the mixture comprising:
a) a physiologic fraction of BMA comprising:
   i) MSPCs present in the physiologic fraction at a level greater than their native level in whole BMA, and
   ii) a depleted level of the first supporting constituent, and
b) an MSG supplement comprising the first supporting constituent, the first supporting constituent being present in the supplement at a level greater than the depleted level of the first supporting constituent in the physiologic fraction.

Because this approach supplements the physiologic fraction with an MSG supplement, it possesses even greater MSG capabilities than the merely concentrated fractions used by Ohgushi. Because the mixture made by this approach possesses a physiologic fraction of BMA having enhanced MSPC levels, it is advantageous over the other prior art composites for all the reasons discussed previously.

Moreover, this mixture may be easily made by simply concentrating MSPCs from whole BMA (by, for example, retaining only the buffy coat from centrifuged BMA) and adding the MSG supplement to the retained MSPC-rich physiologic fraction. The MSG supplement may be obtained from any number of sources and may be in any number of forms. For example, the MSG supplement may be obtained from an allogenic source, from the patient's whole blood, or from the patient's BMA.

Depending upon the method used to concentrate the MSPCs, each of the above-named native supporting constituents of BMA may represent the depleted constituent of the present invention. As the presence of these native depleted constituents is normally considered to be desirable for MSG, in some embodiments, the volumetric amounts of the first and second components are selected so that, when the first and second components are combined, the total amount of the depleted constituent in the resulting composite is at least 25% of its native level, as determined on a volumetric basis. For the purposes of the present invention, when the total amount of the depleted constituent in the resulting composite is at least 25% of its native level, the depleted constituent is at a "near-native" level. Preferably, the total amount of the depleted constituent in the composite is at least 33% of its native level, more preferably at least 50%.

Preferably, this MSG mixture is loaded into a carrier matrix to provide a musculoskeletogenic MSG graft composite made from whole bone marrow aspirate BMA having native levels of musculoskeletal progenitor cells MSPCs and a first supporting constituent, the composite comprising:
a) a physiologic fraction of BMA comprising:
  i) MSPCs present in the physiologic fraction at a level greater than their native level in whole BMA, and
  ii) a depleted level of the first supporting constituent, and
b) an MSG supplement comprising the first supporting constituent, the first supporting constituent being present in the supplement at a level greater than the depleted level of the first supporting constituent in the physiologic fraction, and.
c) a porous biocompatible implantable matrix having an average pore size of at least 20 µm.

In a first preferred embodiment directed to replenishing depleted native constituents, whole BMA is manipulated (preferably by high rpm centrifugation) to form a fractionated BMA, and the RBC fraction, the plasma fraction and the platelet button are removed from the fractionated BMA to leave a first component consisting essentially of the nucleated bone marrow cell NBMC fraction of the whole buffy coat fraction (that comprises high levels of MSPCs). Since the RBC, plasma and platelet bands comprise about 90-95% volume percent ("vol %") of the BMA, the MSPC level in the first component has been increased about 9-19 fold over its native level in the BMA. However, this first component is also devoid of important constituents that typically reside in the plasma and platelet fractions of whole BMA and may play a role in MSG, including but not limited to fibrinogen (found in the plasma fraction), plasma-based soluble growth factors, and growth factors released from platelets during the platelet release reaction, such as PDGF. Each of these constituents are believed to play a role in MSG.

Accordingly, in one embodiment, the second component of the composite comprises platelets at a level greater than that present in the first component. When these components are mixed, the level of platelets in the composite is greater than that initially found in the first component.

Alternatively, the second component of the composite comprises a free platelet-derived growth factor at a level greater than that present in the first component. When these components are mixed, the level of the free platelet-derived factor in the composite is greater than that initially found in the first component.

Preferably, the second component of this embodiment has a platelet or platelet-derived growth factor level at least equal to that of its native level. In a first case, the second component consists essentially of whole bone marrow aspirate, which contains both platelets and platelet-derived factors essentially at their native levels. When this second component is mixed with the buffy coat component, the platelets and platelet-derived factor levels in the composite may be at near-native levels. In a second case, the second component is platelet rich plasma (PRP). When this component is mixed with the buffy coat component, the platelet or platelet-derived factor level in the composite may equal or exceed that of native BMA.

In preferred embodiments, the volumetric ratio of the first component to the second component is between 1:1 and 1:20, more preferably between 1:3 and 1:10. Optionally, if platelets are selected as the MSG supplement, they can be resuspended in volumes of plasma (to from PRP) prior to mixing it with the isolated buffy coat fraction.

In a second preferred embodiment, BMA is manipulated (preferably by centrifugation) to form a fractionated BMA. Next, not only the RBC and plasma fractions but also an MSPC-poor fraction of the buffy coat are removed from the fractionated BMA (as per Budenz) to form a first component comprising enriched MSPCs. Since the RBC, plasma, and the removed buffy coat fractions can comprise at least about 95-99 volume percent ("vol %") of the BMA, the MSPC level in the first component may be increased at least 20 fold (and often as much as 50 fold) over its native level in the BMA, and has been enriched relative to the other NBMCs such as HC. However, this first component is also depleted of important constituents that typically reside in the whole buffy coat fraction and may play a role in MSG, including but not limited to the certain NBMCs and buffy coat proteins and molecules present primarily in the removed buffy coat portion. For example, one NBMC which may be depleted during MSPC enrichment is HC. These depleted buffy coat proteins, molecules and HCs may play a role in MSG.

Accordingly, in one embodiment, the second component of the composite comprises HCs present in the second component at a level greater than that present in the first component. When these components are mixed, the level of HCs in the composite is greater than that found in the first component.

Alternatively, the second component of the composite comprises a physiologic fraction of BMA comprising buffy coat-derived proteins at a level greater than that present in the first component. When these components are mixed, the level of buffy coat derived-proteins in the composite is greater than that found in the first component.

Preferably, the second component of this embodiment has an HC or buffy coat protein level at least equal to that of its native level. In a first case, the second component is preferably whole bone marrow aspirate, which contains both HC and buffy coat proteins essentially at their native levels. When this second component is mixed with the buffy coat component, the HC and buffy coat protein levels in the composite may be at near native levels. In a second case, the second component is a phyiologic buffy coat fraction, which typically has buffy coat protein and HC levels that exceed those of the native whole BMA by a factor of about 9-19. When this second component is mixed with the MSPC-enriched first component, the buffy coat protein and HC levels in the composite may equal or exceed those in native BMA.

This preferred process results in a suspension comprising whole bone marrow aspirate or whole buffy coat (which inherently contains its native levels of non-MSPC NBMCs believed to be necessary for adequately supporting the osteogenic activity of MSPC) having an enriched level of MSPCs.

In preferred embodiments, the volumetric ratio of the first component to the second component is between 1:1 and 1:20, preferably between 1:3 and 1:10.

In preferred embodiments in which the physiologic fraction of BMA has enriched MSPC levels, the enriched MSPC fraction is obtained by centrifuging bone marrow aspirate and then isolating the MSPC-rich fraction within the NBMC fraction. In some embodiments an MSPC-rich fraction may be obtained by isolating the portion of the centrifuged BMA having a density of between 1.06 g/cc and 1.09 g/cc, more preferably between 1.07 g/cc and 1.08 g/cc. The resulting suspension comprises a physiologic fraction of BMA consisting essentially of constituents having a minimum density of about 1.06 g/cc and a maximum density of about 1.09 g/cc.

In such isolated fractions, the MSPC concentration is typically between 1,000 and 1,000,000 cells per milliliter (ml). This enriched MSPC fraction can then be mixed with MSG supplements having higher (and preferably native) levels of HCs, (such as fresh bone marrow aspirate) to produce a suspension having enriched levels of MSPCs and near native levels of HCs. In one preferred embodiment, about 1-5 parts by volume of a first physiologic fraction containing a highly enriched MSPC fraction is added to about 5-9 parts by volume of a suspension having native levels of HCs to produce a suspension having both enriched levels of MSPCs and near-native levels of HCs. In one especially preferred embodiment, the first physiologic fraction is obtained by density gradient centrifugation, and so contains about an MSPC level about 10-fold higher than the MSPC level in native BMA, and the suspension is whole bone marrow aspirate. These two suspensions are mixed in an about 1:9 ratio by volume to obtain a novel suspension comprising a) about 0.1% MSPC present at 110-400% of its native level, and b) about 95% HC present at about 90% of its native level.

In a third preferred embodiment, whole BMA is manipulated to form a fractionated BMA, and at least part of the plasma fraction is removed from the fractionated BMA to form a first component comprising a concentrated buffy coat fraction (which comprises MSPCs). Since whole plasma comprises about 50 volume percent ("vol %") of the BMA, the MSPC level in the first component has been increased up to about 2-fold over its native level in the BMA. However, this first component is also depleted of important constituents that typically reside in the plasma fraction and may play a role in MSG, including but not limited to fibrinogen and other plasma proteins such as soluble growth factors.

Accordingly, in one embodiment, the second component of the composite comprises fibrinogen at a level greater than that present in the first component. When these components are mixed, the level of fibrinogen in the composite is greater than that initially found in the first component. Preferably, the second component comprising fibrinogen is a physiologic fraction of BMA or whole blood.

Alternatively, the second component of the composite comprises a physiologic fraction of BMA comprising a plasma-derived soluble growth factor at a level greater than that present in the first component. When these components are mixed, the level of the plasma-derived soluble growth factor in the composite is greater than that initially found in the first component.

Preferably, the second component of this embodiment has a fibrinogen or plasma-derived soluble growth factor level at least equal to that of its native level. In a first case, the second component comprises whole bone marrow aspirate, which contains both fibrinogen and soluble growth factors at about their native levels (due to the addition of anti-coagulants). When this second component is mixed with the buffy coat first component, the fibrinogen and soluble growth factor levels in the composite may approach those present in native BMA. In a second case, the second component is whole plasma from which water has been extracted, and thereby contains concentrated fibrinogen and concentrated soluble growth factor. When this component is mixed with the concentrated buffy coat of the first component, the fibrinogen or plasma-derived soluble growth factor level in the composite may equal or exceed that of native BMA.

In a particularly preferred case of this embodiment, BMA is centrifuged to form a fractionated BMA, and not only the plasma fraction but also the RBC fraction are substantially removed from the fractionated BMA to leave a first component consisting essentially of a whole buffy coat portion (which comprises high levels of MSPCs and includes platelets). Since the RBC and plasma fractions comprise about 90-95% volume percent ("vol %") of the BMA, the MSPC level in the first component has been increased about 9-19 fold over its native level in the BMA.

Accordingly, also in accordance with the present invention, there is provided a preferred process for producing autologous bone graft materials from whole BMA having a native level of nuclear bone marrow cells NBMC, comprising the steps of:
  a) providing a suspension comprising a concentrated buffy coat fraction having a NBMC level at least 2 fold greater (preferably, between about 9 and about 19 fold greater) than its native level, and
  b) mixing the first component with a second component comprising (and preferably consisting essentially of) whole BMA.

This process results in a suspension of whole BMA (which inherently contains its native levels of fibrinogen and growth factors believed to be necessary for adequately supporting the osteogenic activity of MSPC) having an enriched level of MSPCs. In preferred embodiments, the volumetric ratio of the first component to the second component is between 1:1 and 1:20, more preferably between 1:3 and 1:10.

Accordingly, there is provided an osteogenic composition for producing autologous bone graft materials from whole BMA having a native level of nuclear bone marrow cells NBMC comprising:
  a) a first component comprising a concentrated buffy coat suspension having a NBMC level at least 2 fold greater (preferably, at least 9-19 fold greater) than its native level, and
  b) a second component comprising (and preferably consisting essentially of) whole BMA.

Preferably, this osteogenic composition is loaded into a carrier matrix to provide a composite for use in autologous bone grafting, comprising:
  a) a suspension comprising:
    i) a concentrated buffy coat suspension having a NBMC level at least 2 fold greater (preferably, at least 9-19 fold greater) than its native level, and
    ii) whole BMA, and
  b) a porous biocompatible implantable matrix having an average pore size of at least 20 µm.

In a third approach, two concentrated fractions of BMA are mixed. Accordingly, there is provided a musculoskeletogenic MSG graft composite made from whole bone marrow aspirate BMA having native levels of musculoskeletal progenitor cells MSPCs and a supporting constituent, comprising:
a) a first fraction of BMA comprising:
  i) MSPCs present in the first fraction at a level greater than their native level in whole BMA, and
  ii) a depleted level of the supporting constituent, and
b) a second fraction of BMA, the second fraction being physiologic and comprising the supporting constituent present in the second fraction at a level greater than its native level in whole BMA,
wherein the first and second fractions of BMA comprise less than whole BMA.

Because the first fraction in this third approach possesses enhanced levels of MSPCs, it has higher levels of this critical MSG constituent than the composites using merely whole BMA as a MSPC source (such as Harada and Walsh). Because this third approach provides a second fraction of BMA, it possesses even more MSG constituents than the merely concentrated composite of Ohgushi. Because the second component of this approach is a fraction of BMA, this graft may contain enhanced levels of the supporting constituents. Such enhanced levels would be higher than those found in other conventional MSPC-rich grafts which provided supplementation using only whole BMA (such as Matsukara and Muschler II).

Although Muschler I and Robey teach supplementing the concentrated MSPC components with selected constituents removed during the MSPC concentration process, each of these references appears to provide only a piecemeal reintroduction of BMA constituents (i.e., reintroducing only certain selected single constituents, such as growth factors or fibrinogen, into the concentrated MSPC composition). Because of this piecemeal approach, the composite material may still lack effective amounts of other constituents also present within BMA which may also play important roles in tissue repair.

This composite may be easily made by simply producing an MSPC-rich fraction from whole BMA (by, for example, producing the MSPC-rich product of Muschler I) and then contacting that product with a physiologic fraction of BMA (produced, for example, by centrifuging the eluted fraction of the first step to obtain PRP).

In the third approach, the first fraction of BMA having enhanced MSPC levels is preferably a physiologic fraction, and more preferably comprises the whole buffy coat fraction. However, in some embodiments, the first fraction need not be physiologic. For example, in some embodiments, BMA is passed over a porous matrix capable of selectively retaining MSPCs, as per Muschler I, to form a first component comprising enriched MSPCs. According to Muschler, this process can enhance the MSPC level in the first component (which includes the substrate) by up to 19 times over its native level in the BMA (if the volume of the matrix material is 10% of the treated BMA volume). However, this first component may also lack important constituents that typically reside in the buffy coat fraction and may play a role in MSG, including but not limited to certain nonadhering NBMCs and nonadhering buffy coat proteins present normally in the buffy coat, and nonadhering proteins normally present in the plasma. For example, one nonadhering NBMC which may be depleted during the Muschler MSPC-enrichment process is the polymorphonuclear leukocyte. One nonadhering plasma protein which may be depleted during this MSPC enrichment process is interleukin-1. These depleted nonadhering buffy coat and plasma proteins and nonadhering NBMCs may play a role in MSG.

Accordingly, in one embodiment, the second component of the composite comprises a physiologic fraction of BMA comprising a nonadhering NBMC at a level greater than that present in the first component. When these components are mixed, the level of the nonadhering NBMCs in the composite is greater than that initially found in the first component.

Alternatively, the second component of the composite comprises a physiologic fraction of BMA comprising a nonadhering buffy coat protein at a level greater than that present in the first component. When these components are mixed, the level of the nonadhering buffy coat protein in the composite is greater than that initially found in the first component. Alternatively, the second component of the composite comprises a physiologic fraction of BMA comprising a nonadhering plasma protein at a level greater than that present in the first component. When these components are mixed, the level of the nonadhering plasma protein in the composite is greater than that initially found in the first component.

Preferably, the second component of this embodiment has a nonadhering NBMC, nonadhering plasma protein or nonadhering buffy coat protein level at least equal to that of its native level. In a first case, the second component is preferably whole bone marrow aspirate, which contains nonadhering HC and nonadhering buffy coat and plasma proteins essentially at their native levels. When this second component is mixed with the enriched MSPC first component, the nonadhering constituent level in the composite may be at near native levels. In a second case, the second component comprises a whole buffy coat fraction, which has nonadhering NBMC and nonadhering buffy coat protein levels which exceed those of the native BMA by a factor of about 9-19. When this component is mixed with the enriched-MSPC first component, the level of nonadhering buffy coat proteins or nonadhering NBMC level in the composite may equal or exceed that of native BMA.

It is further believed that the extent to which both MSPCs and other MSG materials within a musculoskeletogeneic composite are bound to the porous matrix may influence the impact those materials play in the chain of events leading to musculoskeletogenesis. In particular, the impact and/or role played by a bioactive material may depend upon whether the bioactive material is a) predominantly bound to the surface of the porous matrix, b) predominantly suspended within the interstices of the porous matrix, or c) both present upon the surface of the porous matrix and suspended within its interstices.

It is believed that the present inventors are the first to tailor the microstructure of musculoskeletogenic composites so that not only soluble growth factors but also the MSG cellular components such as MSPCs are provided in a predetermined free, bound or partially bound state depending upon their desired availability in producing specific musculoskeletogenic responses.

In general, when a bioactive material is freely suspended within the matrix interstices, it is available essentially immediately for MSG activity within the porous matrix. Free suspension of that material may be desirable when that bioactive material plays a role in the initial stages of musculoskeletogenesis. For example, certain bioactive materials play a desirable role in an early stage mechanism (such as chemotaxis), and so it may be desirable for at least a portion of that material to be freely suspended within the matrix interstices. When the material is in this freely suspended state, it is essentially immediately available to act as a chemotactic agent. A composite having a porous matrix and a freely suspended bioactive material therein can be made by, for example, mixing the bioactive material with an activated clotting agent prior to its exposure to the matrix. The clotting process will essentially trap the bioactivate material within the clot, thereby preventing the bioactive material from becoming bound to the porous matrix.

In some embodiments, the MSPCs are suspended within the interstices of the porous matrix.

Therefore, in some embodiments, there is provided a musculoskeletogenic MSG graft composite made from whole bone marrow aspirate BMA having a native level of musculoskeletal progenitor cells MSPCs, comprising:
a) a porous matrix having interstices, and
b) MSPCs present at a level greater than their native level in whole BMA,
wherein the MSPCs are suspended within the interstices of the matrix.

If the free suspension of an MSG constituent within the interstices of the porous matrix is desired, the constituent may be first mixed with a gel-forming material (such as a fibrinogen containing solution or a collagen solution), and the mixture be allowed to gel. This pre-gelled mixture comprising a gel material having an MSG constituent freely suspended therein may then be mixed with porous matrix material.

Similarly, if it is desired that a bioactive material play a role in a later stage mechanism then it may be desirable for that material to be bound to the matrix surface. When the material is in this bound state, it is not immediately available and becomes available only upon its release from the porous matrix surface.

If a composite having a porous matrix and a bound bioactive material thereon is desired, it can be made by, for example, percolating an MSG constituent through the porous matrix, provided the MSG constituent has a surface chemistry amenable to its being bound to the surface of the porous matrix.

For the purposes of the present invention, constituents which are "substantially bound" to the porous matrix includes constituents which are either directly or indirectly bound to the surface of the porous matrix. Examples of indirect binding include binding homologous or heterologous molecules.

In still other circumstances, it may be desired that one portion of the bioactive material be freely suspended and another portion of that same bioactive material be bound. Such a mixture of bound and freely suspended states may be desirable when the bioactive material plays roles in both early and late stages of musculoskeletogenesis. For the purposes of the present invention, when between 20% and 80% of a bioactive material is bound to the porous matrix, it is considered to be "partially bound" to the matrix.

If a composite having a porous matrix and a partially bound bioactive material is desired, it can be made by, for example, formulating a low viscosity suspension having both the bioactive material and a gelling agent, exposing the suspension to the porous matrix, and tailoring the extent of binding by adjusting the gelling time. The extent of binding in such a system will depend upon the amount of time it takes for the mobility-reducing gel to form. For example, if fibrin glue is chosen as the gel, the time to gel can be easily adjusted by adjusting the amount of thrombin used in the clotting reaction. If a composite having a greater degree of bound bioactive material is desired, then a small amount of thrombin is used, thereby lengthening the clotting time, typically to at least 2.1 minutes. If a composite having a lesser degree of bound bioactive material is desired, then a greater amount of thrombin is used, thereby reducing the clotting time, typically to no more than 1.9 minutes.

Therefore, in some embodiments, more than 80% of the MSPC component is bound to the porous matrix. In other embodiments, more than 80% of the MSPC component of the physiologic fraction having enhanced MSPC levels is adhered to the porous matrix, with the remainder being essentially freely suspended in the interstices of the matrix. In other embodiments, between 20% and 80% of the MSPC component of the physiologic fraction having enhanced MSPC levels is adhered to the porous matrix, with the remainder being essentially freely suspended in the interstices of the matrix.

Therefore, in some embodiments, there is provided a musculoskeletogenic MSG graft composite made from whole bone marrow aspirate BMA having a native level of musculoskeletal progenitor cells MSPCs, comprising:
a) a porous matrix having an average pore size of at least 20 um,
b) MSPCs present within a first pre-clotted clot material, the material being present within the interstices of the pores of the matrix.

Preferably, this further comprises c) a physiologic fraction of BMA having the MSPCs substantially removed therefrom, the fraction being present within the interstices of the porous matrix. In some embodiments, the fraction comprises an in-situ formed clot, wherein the in-situ formation of the clot is completed in either no more than 1.9 minutes or at least 2.1 minutes. In some embodiments, the fraction comprises a second pre-clotted clot material. In others, the composite further comprises c) a physiologic fraction of BMA, the fraction being present within the interstices of the porous matrix, wherein the MSPCs are present as a component of the fraction.

In some embodiments, there is provided a musculoskeletogenic MSG graft composite made from whole bone marrow aspirate BMA having a native level of musculoskeletal progenitor cells MSPCs, comprising:
a) a porous matrix having an average pore size of at least 20 um,
b) a first in-situ clotted clot material present within the interstices of the pores, and
c) MSPCs present within the in-situ clotted clot material, wherein the clotting of the in-situ clotted clot material occurred for at least 2.1 minutes.

Preferably, the composite further comprises d) a physiologic fraction of BMA having MSPCs substantially removed therefrom. The composite may also further comprise d) a physiologic fraction of BMA, the fraction being present within the first in-situ clotted clot material, wherein the MSPCs are present as a component of the physiologic fraction.

In some embodiments, there is provided a musculoskeletogenic MSG graft composite made from whole bone marrow aspirate BMA having a native level of musculoskeletal progenitor cells MSPCs, comprising:
a) a porous matrix having an average pore size of at least 20 um,
b) a first in-situ clotted clot material present within the interstices of the pores, and
c) MSPCs present within the in-situ clotted clot material, wherein the gellation of the in-situ gel material occurred for no more than 1.9 minutes.

Preferably, the composite further comprises d) a physiologic fraction of BMA having MSPCs substantially removed therefrom. It also may further comprise d) a physiologic fraction of BMA, the fraction being present within the first in-situ clotted clot material, wherein the MSPCs are present as a component of the fraction.

In some embodiments, there is provided a musculoskeletogenic MSG graft composite made from whole bone marrow aspirate BMA having a native level of musculoskeletal progenitor cells MSPCs, comprising:
a) a porous matrix having an average pore size of at least 20 um,
b) an in-situ clotted clot material present within the interstices of the pores, and
c) MSPCs predominantly bound to the surface of the matrix,
wherein the clot material comprises a physiologic fraction of BMA having the MSPCs substantially removed therefrom.

In some embodiments, there is provided a musculoskeletogenic MSG graft composite made from whole bone marrow aspirate BMA having a native level of musculoskeletal progenitor cells MSPCs, comprising:
a) a porous matrix having an average pore size of at least 20 um,
b) a pre-clotted clot material present within the interstices of the pores, and
c) MSPCs present within the interstices of the pores,
wherein the clot material comprises a physiologic fraction of BMA having the MSPCs removed therefrom.

Preferably, the MSPCs are predominantly bound upon the surface of the porous matrix. In some embodiments, the MSPCs are predominantly present within the pre-clotted clot material, or predominantly present in an in-situ formed clot, wherein the clotting of the in-situ clotted clot material occurred for at least 2.1 minutes, or for no more than 1.9 minutes.

In some embodiments, there is provided, a musculoskeletogenic MSG graft composite made from whole bone marrow aspirate BMA having a native level of musculoskeletal progenitor cells MSPCs, comprising:
a) a porous matrix having an average pore size of at least 20 um,
b) a pre-clotted clot material present within the interstices of the pores,
c) MSPCs predominantly present within the clot material, and
d) an MSG supplement predominantly bound to the surface of the matrix.

Preferably, the composite further comprises e) a physiologic fraction of BMA having MSPCs removed therefrom. Preferably, the composite further comprises f) a first in-situ clotted clot material, wherein the physiologic fraction is present within the first in-situ clotted clot material.

In some embodiments, there is provided, a musculoskeletogenic MSG graft composite made from whole bone marrow aspirate BMA having a native level of musculoskeletal progenitor cells MSPCs, comprising:
a) a porous matrix having an average pore size of at least 20 um,
b) an in-situ clotted clot material present within the interstices of the pores,
c) MSPCs predominantly present within the clot material, and
d) an MSG supplement predominantly bound to the surface of the matrix.

Preferably, the composite further comprises e) a physiologic fraction of BMA having MSPCs substantially removed therefrom. In other embodiments, the composite further comprises e) a physiologic fraction of BMA, the physiologic fraction being present within the in-situ clotted clot material, wherein the MSPCs are present as a component of the physiologic fraction.

In some embodiments, there is provided a musculoskeletogenic MSG graft composite made from whole bone marrow aspirate BMA having a native level of musculoskeletal progenitor cells MSPCs, comprising:
a) a porous matrix having an average pore size of at least 20 um,
b) MSPCs predominantly bound to the surface of the matrix, and
c) platelet rich plasma PRP supplement predominantly bound to the surface of the matrix.

Preferably, the composite further comprises d) a physiologic fraction of BMA having MSPCs removed therefrom.

In some embodiments, there is provided a musculoskeletogenic MSG graft composite made from whole bone marrow aspirate BMA having a native level of musculoskeletal progenitor cells MSPCs, comprising:
a) a porous matrix having an average pore size of at least 20 um,
b) an in-situ clotted clot material present within the interstices of the pores,
c) an MSG supplement predominantly bound to the surface of the matrix,
d) a physiologic fraction of BMA having the MSPCs removed therefrom,
wherein the physiologic fraction is present within the in-situ clotted clot material.

Preferably, the composite further comprises e) MSPCs, wherein the MSPCs are predominantly bound upon the surface of the porous matrix. In other embodiments, the composite further comprises e) MSPCs and f) a pre-clotted clot material, wherein the MSPCs are predominantly present within the pre-clotted clot material.

In some embodiments, there is provided a musculoskeletogenic MSG graft composite made from whole bone marrow aspirate BMA having a native level of musculoskeletal progenitor cells MSPCs, comprising:
a) a porous matrix having an average pore size of at least 20 um,
b) a pre-clotted clot material present within the interstices of the pores,
c) an MSG supplement predominantly bound to the surface of the matrix,
d) a physiologic fraction of BMA having the MSPCs removed therefrom,
wherein the fraction is present within the in-situ clotted clot material.

Preferably, the composite further comprises e) MSPCs, wherein the MSPCs are predominantly bound upon the surface of the porous matrix. In other embodiments, the composite further comprises e) MSPCs and f) an in-situ clotted clot material, wherein the MSPCs are predominantly present within the in-situ gelled gel material. In other embodiments, the composite further comprises e) a physiologic fraction of BMA, the fraction being present within the pre-clotted clot material, wherein the MSPCs are present as a component of the fraction.

In some embodiments, there is provided a musculoskeletogenic MSG graft composite made from whole bone marrow aspirate BMA having a native level of musculoskeletal progenitor cells MSPCs, comprising:
a) a porous matrix having an average pore size of at least 20 um,
b) a pre-clotted clot material present within the interstices of the pores,
c) MSPCs predominantly present within the clot material,
d) an in-situ clotted clot material present within the interstices of the pores, and
e) an MSG supplement present within the in-situ clotted clot material.

Preferably, the composite further comprises e) a physiologic fraction of BMA having MSPCs removed therefrom. Preferably, the composite further comprises f) a first in-situ clotted clot material, wherein the fraction is present within the first in-situ clotted clot material.

In some embodiments, there is provided a musculoskeletogenic MSG graft composite made from whole bone marrow aspirate BMA having a native level of musculoskeletal progenitor cells MSPCs, comprising:
a) a porous matrix having an average pore size of at least 20 um,
b) a first in-situ clotted clot material present within the interstices of the pores,
c) an MSG supplement present within the in-situ clotted clot material, and
d) MSPCs present within the in-situ clotted clot material, wherein the clotting of the in-situ clotted clot material occurred for no more than 1.9 minutes.

Preferably, the composite further comprises e) a physiologic fraction of BMA having MSPCs removed therefrom. In other embodiments, the composite of claim C11 further comprising e) a physiologic fraction of BMA, the fraction being present within the in-situ clotted clot material, wherein the MSPCs are present as a component of the fraction.

In some embodiments, there is provided, a musculoskeletogenic MSG graft composite made from whole bone marrow aspirate BMA having a native level of musculoskeletal progenitor cells MSPCs, comprising:
a) a porous matrix having an average pore size of at least 20 um,
b) a first in-situ clotted clot material present within the interstices of the pores,
c) an MSG supplement present within the in-situ clotted clot material, and
d) MSPCs present within the in-situ clotted clot material, wherein the gellation of the in-situ clotted clot material occurred for at least 2.1 minutes.

Preferably, the composite of claim C21 further comprising e) a physiologic fraction of BMA having MSPCs removed therefrom. In some embodiments, the composite further comprises e) a physiologic fraction of BMA, the fraction being present within the in-situ clotted clot material, wherein the MSPCs are present as a component of the fraction.

In some embodiments, there is provided a musculoskeletogenic MSG graft composite made from whole bone marrow aspirate BMA having a native level of musculoskeletal progenitor cells MSPCs, comprising:
a) a porous matrix having an average pore size of at least 20 um,
b) an in-situ clotted clot material present within the interstices of the pores,
c) an MSG supplement present within the in-situ clotted clot material,
d) a pre-clotted clot material present within the interstices of the pores, and
e) a physiologic fraction of BMA having the MSPCs removed therefrom,
wherein the fraction is present within the pre-clotted clot material.

Preferably, the composite further comprises e) MSPCs, wherein the MSPCs are predominantly bound upon the surface of the porous matrix. In other embodiments, the composite further comprises e) MSPCs, wherein the MSPCs are present as a component of the fraction. In other embodiments, the composite further comprises e) MSPCs, wherein the MSPCs are present within the in-situ clotted clot material.

In some embodiments, there is provided a musculoskeletogenic MSG graft composite made from whole bone marrow aspirate BMA having a native level of musculoskeletal progenitor cells MSPCs, comprising:
a) a porous matrix having an average pore size of at least 20 um,
b) an in-situ clotted clot material present within the interstices of the pores,
c) an MSG supplement present within the in-situ clotted clot material, and
d) a physiologic fraction of BMA having the MSPCs removed therefrom,
wherein the physiologic fraction is present within the in-situ clotted clot material.

In some embodiments, there is provided a musculoskeletogenic MSG graft composite made from whole bone marrow aspirate BMA having a native level of musculoskeletal progenitor cells MSPCs, comprising:
a) a porous matrix having an average pore size of at least 20 um,
b) an in-situ clotted clot material present within the interstices of the pores,
c) an MSG supplement comprising a physiologic fraction of BMA, the MSG supplement being present within the in-situ clotted clot material, and
e) MSPCs predominantly bound to the surface of the porous matrix.

In some embodiments, there is provided a musculoskeletogenic MSG graft composite made from whole bone marrow aspirate BMA having a native level of musculoskeletal progenitor cells MSPCs, comprising:
a) a porous matrix having an average pore size of at least 20 um,
b) an in-situ clotted clot material present within the interstices of the pores,
c) an MSG supplement free of BMA-derived constituents, and
d) MSPCs predominantly bound to the surface of the porous matrix.

In some embodiments, there is provided a musculoskeletogenic MSG graft composite made from whole bone marrow aspirate BMA having a native level of musculoskeletal progenitor cells MSPCs, comprising:
a) a porous matrix having an average pore size of at least 20 um,
b) a pre-clotted clot material present within the interstices of the pores,
c) MSPCs predominantly present within the clot material, and
d) an MSG supplement present within the clot material.

Preferably, the composite further comprises e) a physiologic fraction of BMA having MSPCs removed therefrom. Preferably, the composite further comprises f) a first in-situ clotted clot material, wherein the fraction is present within the first in-situ gelled material. In other embodiments, the composite further comprises e) a physiologic fraction of BMA, the fraction being present within the pre-clotted clot material, wherein the MSPCs are present as a component of the fraction.

In some embodiments, there is provided a musculoskeletogenic MSG graft composite made from whole bone marrow aspirate BMA having a native level of musculoskeletal progenitor cells MSPCs, comprising:
a) a porous matrix having an average pore size of at least 20 um,
b) a pre-clotted clot material present within the interstices of the pores,
c) an MSG supplement present within the clot material,
d) an in-situ clotted clot material present within the interstices of the pores, and
f) MSPCs present within the in-situ clotted clot material.

Preferably, the composite further comprises f) a physiologic fraction of BMA having MSPCs removed therefrom. Preferably, the fraction is present within the first in-situ clotted clot material. In some embodiments, the composite further comprises f) a physiologic fraction of BMA, the fraction being present within the pre-clotted clot material, wherein the MSPCs are present as a component of the fraction.

In some embodiments, there is provided a musculoskeletogenic MSG graft composite made from whole bone marrow aspirate BMA having a native level of musculoskeletal progenitor cells MSPCs, comprising:
a) a porous matrix having an average pore size of at least 20 um,
b) a pre-clotted clot material present within the interstices of the pores,
c) an MSG supplement present within the clot material,
d) an in-situ clotted clot material present within the interstices of the pores,
e) a physiologic fraction of BMA having MSPCs removed therefrom and present within the in-situ clotted clot material, and
f) MSPCs predominantly bound to the surface of the matrix In some embodiments, there is provided a musculoskeletogenic MSG graft composite made from whole bone marrow aspirate BMA having a native level of musculoskeletal progenitor cells MSPCs, comprising:
- a) a porous matrix having an average pore size of at least 20 um,
- b) a pre-clotted clot material present within the interstices of the pores,
- c) an MSG supplement comprising a physiologic fraction of BMA, the MSG supplement being present within the pre-clotted clot material, and
- d) MSPCs predominantly bound to the surface of the porous matrix.

In some embodiments, there is provided a musculoskeletogenic MSG graft composite made from whole bone marrow aspirate BMA having a native level of musculoskeletal progenitor cells MSPCs, comprising:
- a) a porous matrix having an average pore size of at least 20 um,
- b) a pre-clotted clot material present within the interstices of the pores,
- c) an MSG supplement predominantly bound to the surface of the matrix,
- d) a physiologic fraction of BMA having the MSPCs removed therefrom, wherein the fraction is present within the in-situ clotted clot material.

In some embodiments, there is provided a musculoskeletogenic MSG graft composite made from whole bone marrow aspirate BMA having a native level of musculoskeletal progenitor cells MSPCs, comprising:
- a) a porous matrix having an average pore size of at least 20 um,
- b) a pre-clotted clot material present within the interstices of the pores,
- c) an MSG supplement present within the pre-clotted clot material, and
- d) a physiologic fraction of BMA having the MSPCs removed therefrom, wherein the fraction is present within the pre-clotted clot material.

EXAMPLES

Six exemplary processes for providing a composite of the present invention are presented below. Each of these examples uses as a starting material a suspension comprising a whole buffy coat. However, other NBMC-rich suspensions, such as any suspension having nucleated bone marrow cells NBMCs present in a cell population at least 3 times greater than their native level, may also be used.

Example 1

In this embodiment, the MSPCs are selectively bound to the porous matrix while a portion of the non-adhering constituents of BMA (i.e., the effluent) are suspended within the interstices of the matrix.

A concentrated whole buffy coat suspension is passed or percolated over a vessel containing the porous matrix in order to retain cells which adhere to the porous matrix. The eluted non-adherent cells of the resuspension (e.g., HCs, POs and RCs) may then be collected and re-percolated over the vessel, or a portion thereof may be added to the porous matrix-adherent cell mixture so as to remain in suspension. The unbound constituents of the suspension may be trapped within the suspension by adding gelling agents such as fibrinogen and gelling activators such as thrombin to the mixture.

The resulting composite contains bound MSG cells (such as enriched MSPCs), bound platelets, freely suspended MSG cells (such as ECs), and freely suspended supporting constituents (such as fibrinogen).

Accordingly, there is provided a process comprising the steps of:
- a) providing a suspension comprising nucleated bone marrow cells NBMCs present in a cell population at least 3 times greater than their native level (preferably substantially free of red blood cells and plasma), and optionally fibrinogen, and optionally a whole BMA component,
- b) combining the suspension with a porous matrix, and, optionally,
- c) adding a clotting activator to the suspension to form a clot within the interstices of the porous matrix.

In other embodiments, there is provided a process comprising the steps of:
- a) providing a suspension comprising a suspension comprising nucleated bone marrow cells NBMCs present in a cell population at least 3 times greater than their native level, the NBMCs comprising MSPCs and non-adherent cells, (and optionally fibrinogen, and optionally a whole BMA component),
- b) passing the suspension through a porous matrix to produce a composite comprising:
  - i) a porous matrix, and
  - ii) MSPCs bound to the porous matrix and
  - iii) an effluent comprising the non-adherent cells,
- c) suspending the effluent within the porous matrix so that the composite further comprises
  - iv) freely suspended non-adherent cells, and, optionally,
- d) adding a clotting activator to the suspension to form a clot.

Example 2

In this embodiment, concentrated MSPCs are freely suspended within the interstices of the porous matrix.

A concentrated whole buffy coat suspension is combined with a platelet rich plasma material and placed in a reaction vessel that allows for clotting of the cell suspension with a platelet rich plasma.

Accordingly, there is provided a process comprising the steps of:
- a) providing a suspension comprising nucleated bone marrow cells NBMCs present in a cell population at least 2 times greater than their native level (preferably substantially free of red blood cells and plasma), the NBMCs comprising MSPCs,
- b) mixing the suspension with a composition comprising an effective amount of fibrinogen to from a clot capable of freely suspending the NBMCs (the composition preferably further comprising growth factors (preferably, PRP), to produce a mixture.

The cell and platelet rich plasma mixture of this embodiment may also be combined with a porous matrix in a reaction vessel. This combination would have the effect of trapping enriched MSPCs in the clotted suspension, but not necessarily in an adherent fashion to the surface of the porous substrate. Accordingly, depending upon the clotting time, the composite could have a freely suspended or partially bound MSPC constituents.

Therefore, preferably, this process further comprises the steps of:
c) combining the mixture with a porous matrix to produce a composite comprising:
   i) a porous matrix,
   ii) a clot material occupying the interstices of the porous matrix, and
   iii) MSPCs freely suspended within the clot material.

Therefore, the is provided a composite comprising:
   i) a porous matrix,
   ii) a clot material occupying the interstices of the porous matrix, and
   iii) MSPCs freely suspended within the clot material.

Also preferably, this process further comprises the steps of:
c) combining the mixture with a porous matrix to produce a composite comprising:
   i) a porous matrix,
   ii) a clot material occupying the interstices of the porous matrix, and
   iii) MSPCs partially bound to the porous matrix.

Example 3

In this embodiment, the MSPCs are bound to the porous matrix while supplements are freely suspended within a clot within the interstices of the porous matrix.

The concentrated whole buffy coat suspension is passed or percolated over a vessel containing the porous matrix in such a way as to allow adherence of the MSPCs to the porous matrix, and the non-adherent population of cells and soluble components is subsequently combined with PRP. This combination is then combined with the porous substrate-NBMC mixture and a clotting activator is added to create a clot which contains both the substrate-NBMC mixture and the bioactive agents derived from platelets.

Accordingly, there is provided a process comprising the steps of:
a) providing a suspension comprising a suspension comprising nucleated bone marrow cells NBMCs present in a cell population at least 3 times greater than their native level, the NBMCs comprising MSPCs and non-adherent cells, (and optionally fibrinogen, and optionally a whole BMA component),
b) passing the suspension through a porous matrix to produce a first composite comprising:
   i) a porous matrix, and
   ii) MSPCs bound to the porous matrix, and
   iii) an effluent comprising the non-adherent cells,
c) combining the effluent with a composition comprising a solution containing fibrinogen (and preferably platelets) to produce a mixture.

Preferably, this process further comprises the steps of:
d) suspending the mixture within the interstices of the porous matrix of the first composite, and, optionally,
e) adding a clotting activator to the mixture to form a second composite comprising:
   i) a porous matrix, and
   ii) MSPCs bound to the porous matrix,
   iii) a fibrin clot within the interstices of the porous matrix, (and optionally)
   iv) growth factors freely suspended within the fibrin clot.

Therefore, there is provided a second composite comprising:
   i) a porous matrix, and
   ii) MSPCs bound to the porous matrix,
   iii) a fibrin clot within the interstices of the porous matrix, (and optionally)
   iv) growth factors freely suspended within the fibrin clot.

Example 4

The concentrated whole buffy coat component is passed over the porous matrix. The adhered MSPC-porous matrix composite is then combined with an aliquot of whole BMA or a physiologic fraction thereof (such as PPP or PRP) so as to entrap the adhered NMBC-substrate composition in a partial clot containing desirable elements of fresh, unfractionated whole bone marrow aspirate. The non-adherent fraction of NBMCs from the original bone marrow isolate may also be added to the NBMC-porous substrate-fresh bone marrow composition.

Accordingly, there is provided a process comprising the steps of:
a) providing a suspension comprising nucleated bone marrow cells NBMCs present in a cell population at least 3 times greater than their native level, the NBMCs comprising MSPCs and non-adherent cells, (preferably being free of red blood cells and plasma), and optionally fibrinogen,
b) passing the suspension through a porous matrix to produce (i) a first composite comprising the matrix and adhered NMBC cells, and (ii) an effluent comprising non-adherent cells,
c) adding whole BMA to the first composite to produce a second composite, and optionally
d) adding the effluent to the second composite.

Preferably, this process further comprises the steps of:
e) adding a clotting activator to the second composite to form a clot.

Example 5

In Muschler II, there is described a process comprising a first step of passing whole BMA through a porous matrix in order to retain and concentrate the MSPCs thereon, and a second step of mechanically mixing the MSPC-porous matrix combination with clotted bone marrow. However, it was found that the mechanical mixing step adversely affected the integrity of the MSPC-porous matrix combination.

Therefore, there is now provided a process comprising the steps of:
a) mixing a porous matrix with clot particles derived from BMA or blood to produce a mixture, and
b) passing BMA through the mixture.

The resulting composite comprises:
a) a porous matrix,
b) a plurality of clot particles, and
c) MSPCs bound to both the surface of the porous matrix and the surfaces of the clot particles.

Because the porous matrix and clot particles are pre-mixed, the MSPCs remain bound to the matrix and clot particle surfaces.

Table III below provides a summary of the disposition of the different bioactive elements of the composite of the present invention produced by the five examples directly above.

Example 6

The objective of this prophetic example is to generate a bone marrow cell-derived graft material that is superior to the in vivo bone-forming characteristics of fresh bone marrow aspirate.

First, a 20 ml sample of human bone marrow is obtained by conventional aspiration techniques. Second, the aspirate is divided into two portions. Portion #1 contains 16 ml of bone marrow aspirate and will be used to generate a buffy coat (i.e., the isolated NBMC portion of the aspirate). Portion #2 contains 4 ml of aspirate and will remain initially unfractionated. Third, a buffy coat is generated by an appropriate density gradient medium, such as centrifugation. After isolating the buffy coat cells of Portion #1 (by, for example, withdrawl of the non-elected fractions via pipette), saline solution is added to the buffy coat portion to resuspend the buffy coat and make up a 16 ml volume. This resuspension should contain a native level of NBMC. Fourth, the resuspended buffy coat and whole BMA suspensions are mixed according to the volumes listed in Table I, and the mixtures are centrifuged to produce fractions of the buffy coat/whole bone marrow cell mixture. The supernatant of this centrifuged mixture is then removed to obtain a concentrated fraction of the buffy coat/whole bone marrow cell mixture. Fifth, the pellet is resuspended with either saline or PRP according to Table I. Assuming that the removal of the plasma and RBC portions effects a 19× enhancement of the buffy coat level, this resuspension should contain concentrated levels of NBMC (i.e., in the neighborhood of 7-16 times native levels of NBMCs). Sixth, the resuspended pellet formulations are loaded into delivery vehicles, and a vaccum is applied to the loaded vehicle to draw out air entrapped within the vehicle. Seventh, in the PRP-containing vehicles, thrombin is added to the vehicles to form clots. Eighth, the implants are surgically implanted.

TABLE III

| Run Number | Buffy Coat Aliquot (ml) | Whole BMA Aliquot (ml) | Saline/PRP Aliquot (ml) | Buffy Coat Concentration |
|---|---|---|---|---|
| 1 | 4 | 0 | 1 | ~16X native |
| 2 | 3 | 0 | 1 | ~15X native |
| 3 | 2 | 0 | 1 | ~13X native |
| 4 | 1 | 0 | 1 | ~10X native |
| 5 | 3 | 1 | 1 | ~12X native |
| 6 | 2 | 1 | 1 | ~10X native |
| 7 | 1 | 1 | 1 | ~07X native |
| 8 | 0 | 1 | 1 | 0.5X native |
| 9 | 0 | 0 | 1 | 0 |

In some embodiments, there is provided a preferred system of disposables for use in combining the desired combination of bioactive components described above. A vessel containing first opening at a first end having a diametersufficient to allow the movement of fluid combination therethrough, and, at a second end, a normally closed valve which is openable to relieve pressure within the vessel when a fluid component moves through the vessel and porosity of the matrix contained therein. This valve may comprise a standard three-way stopcock. Alternatively, a filter having a porosity sufficiently fine to allow passage of air but not cellular material (e.g., a 0.22 micron filter) may be used instead of the valve as a way of maintaining a sterile environment within the vessel. In addition, the use of the filter insures that the flow of cells therethrough is prevented. Accordingly, this embodiment allows for the introduction of a solution into the vessel containing the porous substrate and relief of atmospheric pressure inside the vessel while retaining sterility.

The ultimate product comprises a porous substrate-NBMC mixture which may optionally be embedded within a bone marrow clot or platelet gel. This graft material may then be extruded from the vessel and implanted directly into the site requiring augmentation of bony tissue.

We claim:

1. A musculoskeletogenic (MSG) graft composite made from whole bone marrow aspirate (BMA), the graft composite consisting of:
    a) a physiologic fraction obtained from centrifugation of whole BMA, consisting essentially of:
        i) musculoskeletal progenitor cells (MSPCs) at a level greater than their native level in whole BMA, and
        ii) red blood cells (RBCs) derived from BMA at a level less than their native level in whole BMA,
        iii) platelets at a level greater than their native level in whole BMA, and
    b) a porous sterile matrix having an $D_{50}$ average pore size of at least 20 μm,
    c) a platelet release agent added in an amount sufficient to cause the release of growth factors from BMA-derived platelets,
wherein the (a) physiologic fraction of BMA and the (c) platelet release agent are contained within the (b) porous sterile matrix, thereby causing release of growth factors from the BMA-derived platelets,
wherein the matrix is demineralized bone matrix and the platelet release agent is thrombin.

2. The composite of claim 1 wherein the MSPCs are present in the physiologic fraction at a level 2 times greater than their native level in whole BMA.

3. The composite of claim 1 wherein the MSPCs are present in the physiologic fraction at a level 5 times greater than their native level in whole BMA.

4. The composite of claim 1 wherein the RBCs derived from BMA are present in the physiologic fraction at a level less than 20% their native level in whole BMA.

5. The composite of claim 1 wherein the porous matrix has a $D_{50}$ average pore size of at least 50 μm.

6. The composite of claim 1 wherein the porous matrix has a $D_{50}$ average pore size of at least 100 μm.

7. The composite of claim 1 wherein the ratio of the physiologic fraction to the matrix is between 1:1 (v/v) and 1:20 (v/v).

* * * * *

UNITED STATES PATENT AND TRADEMARK OFFICE
CERTIFICATE OF CORRECTION

| | |
|---|---|
| PATENT NO. | : 8,313,742 B2 |
| APPLICATION NO. | : 10/109946 |
| DATED | : November 20, 2012 |
| INVENTOR(S) | : Kadiyala et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1062 days.

Signed and Sealed this
Eleventh Day of November, 2014

Michelle K. Lee
*Deputy Director of the United States Patent and Trademark Office*